United States Patent
Szabóné Ordasi et al.

(10) Patent No.: US 10,500,202 B2
(45) Date of Patent: Dec. 10, 2019

(54) PHARMACEUTICAL FORMULATION CONTAINING TADALAFIL

(71) Applicant: Druggability Technologies IP Holdco Limited, Msida (MT)

(72) Inventors: Betti Szabóné Ordasi, Budapest (HU); Tamás Jordán, Öcsöd (HU); Richárd Balázs Kárpáti, Tatabánya (HU); Andrea Ujhelyi, Nyiregyhaza (HU); Tamás Solymosi, Békéscsaba (HU); Hristos Glavinas, Szeged (HU); Genovéva Filipcsei, Budapest (HU)

(73) Assignee: Druggability Technologies IP Holdco Limited, Msida (MT)

( * ) Notice: Subject to any disclaimer, the term of this patent is extended or adjusted under 35 U.S.C. 154(b) by 0 days.

(21) Appl. No.: 15/827,417

(22) Filed: Nov. 30, 2017

(65) Prior Publication Data

US 2018/0161325 A1 Jun. 14, 2018

Related U.S. Application Data

(60) Provisional application No. 62/502,157, filed on May 5, 2017, provisional application No. 62/438,539, filed on Dec. 23, 2016, provisional application No. 62/428,309, filed on Nov. 30, 2016.

(51) Int. Cl.
| | | |
|---|---|---|
| *A61K 31/4985* | (2006.01) | |
| *A61P 15/10* | (2006.01) | |
| *A61P 13/08* | (2006.01) | |
| *A61P 9/12* | (2006.01) | |
| *A61P 21/00* | (2006.01) | |
| *A61K 47/20* | (2006.01) | |
| *A61K 47/32* | (2006.01) | |
| *A61K 9/16* | (2006.01) | |
| *A61K 9/19* | (2006.01) | |

(52) U.S. Cl.
CPC ........ *A61K 31/4985* (2013.01); *A61K 9/1617* (2013.01); *A61K 9/1635* (2013.01); *A61K 9/1682* (2013.01); *A61K 9/19* (2013.01); *A61K 47/20* (2013.01); *A61K 47/32* (2013.01); *A61P 9/12* (2018.01); *A61P 13/08* (2018.01); *A61P 15/10* (2018.01); *A61P 21/00* (2018.01)

(58) Field of Classification Search
CPC .... A61K 31/4985; A61K 47/20; A61K 47/32; A61K 9/1617; A61K 9/1635; A61K 9/1682; A61K 9/19; A61P 13/08; A61P 15/10; A61P 21/00; A61P 9/12
See application file for complete search history.

(56) References Cited

U.S. PATENT DOCUMENTS

| | | | |
|---|---|---|---|
| 7,863,274 B2 * | 1/2011 | Tung | C07D 317/54 514/250 |
| 2007/0004745 A1 | 1/2007 | Pickett | |
| 2007/0104792 A1 * | 5/2007 | Jenkins | A61K 9/14 424/489 |
| 2016/0067246 A1 | 3/2016 | Victor | |

FOREIGN PATENT DOCUMENTS

| | | |
|---|---|---|
| WO | 2012085927 | 6/2012 |
| WO | 2018102572 | 6/2018 |

OTHER PUBLICATIONS

Mao D et al., Rapid screening of sildenafil and tadalafil adulterated in healthcare products by Micro-Raman spectroscopy, Journal of Raman spectroscopy, vol. 43, Issue 12, Dec. 2012, pp. 1985-1990.
Trefi S, et al., Analysis of illegally manufactured formulations of tadalafil (Cialis) by 1H NMR, 2D DOSY 1H NMR and Raman spectroscopy, J Pharm Biomed Anal. May 12, 2008;47(1):103-113.
United States Patent and Trademark Office, International Search Report and Written Opinion of the International Searching Authpority, dated Feb. 14, 2018 for PCT/US17/63992.
CIALIS Prescribing Information, Revised Oct. 2011, 32 pages.
International Application No. PCT/US2017/063992; International Preliminary Report on Patentability, dated Jun. 13, 2019; 9 pages.

* cited by examiner

*Primary Examiner* — Michael B. Pallay
(74) *Attorney, Agent, or Firm* — Dennis A. Bennett; Brock D. Levin; Lauren L. Stevens (57) ABSTRACT

Disclosed herein are pharmaceutical compositions comprising Tadalafil, or a salt, or derivatives thereof and pharmaceutical excipients, processes for the preparation thereof, and pharmaceutical compositions containing them. The pharmaceutical compositions have improved physicochemical properties that provide faster onset of action for the treatment of erectile dysfunction.

9 Claims, 8 Drawing Sheets

Figure 1.

| | | Secondary pharmaceutical excipient | | | | | | | | | | | | | | | |
|---|---|---|---|---|---|---|---|---|---|---|---|---|---|---|---|---|
| | | SDS | DSS | CPC | D-Mannitol | Citric acid | NaOAc | SDC | NONE | Kolliocar IR | Poloxamer 335 | Lactose | Poloxamer 407 | Solutol HS15 | Trehalose | TPGS | Meglumine |
| Primary pharmaceutical excipient | TPGS | - | - | - | + | - | - | - | + | + | - | - | + | - | - | - | + |
| | Poloxamer 338 | - | - | - | - | - | - | - | - | - | - | + | - | - | - | - | - |
| | Poloxamer 335 | - | - | - | + | - | - | - | - | + | - | - | - | - | - | - | - |
| | Poloxamer 407 | - | - | - | - | - | - | - | - | - | - | - | - | - | - | - | - |
| | Poloxamer 188 | - | - | - | - | - | - | - | - | - | - | - | - | - | - | - | - |
| | Copovidone | + | + | + | + | - | - | + | - | - | - | - | + | - | - | - | + |
| | Soluplus | - | - | - | - | - | - | - | - | - | - | - | - | - | - | - | - |
| | Plasdone K-12 | - | + | - | - | - | - | - | - | - | - | - | - | - | - | - | - |
| | PEOX50 | + | + | - | - | - | - | - | - | - | - | + | - | - | - | - | - |
| | Gelucire 44/14 | - | - | - | - | - | - | - | - | - | - | - | - | - | - | - | - |
| | PEG6000 | - | - | - | - | - | - | - | - | - | - | - | - | - | - | - | - |
| | Tetronic 1107 | - | - | - | - | - | - | - | - | - | - | - | - | + | - | - | - |
| | PEOX200 | + | + | - | - | - | - | - | + | + | - | - | + | - | - | - | - |
| | PEG2000 | - | - | - | - | - | - | - | - | - | - | - | - | - | - | - | - |
| | Klucell EF | - | + | + | + | - | - | - | - | - | + | - | - | - | - | - | - |
| | Klucell LF | + | + | + | + | - | - | - | - | - | - | + | - | - | - | - | + |
| | PEOX500 | + | + | - | - | - | - | - | - | - | - | - | - | - | - | - | - |
| | Eudragit EPO | - | - | - | - | - | - | - | - | - | - | - | - | - | - | - | - |
| | HPMCAS | - | - | + | - | - | - | - | - | - | - | + | - | - | + | - | - |
| | NONE | - | - | - | - | - | - | - | - | - | - | - | - | - | - | - | - |
| | + redispersable solid Tadalafil pharmaceutical in ultrapurified water<br>- non-redispersable solid Tadalafil pharmaceutical in ultrapurified water | | | | | | | | | | | | | | | | |

Figure 2.

| Primary pharmaceutical excipient | Secondary pharmaceutical excipient | Redispersibility | PAMPA permability (x10$^{-6}$ cm/s) |
|---|---|---|---|
| Copovidone | DSS | + | 6.88 |
| Klucell LF | SDS | - | 2.70 |
| Copovidone | SDS | + | 7.36 |
| Copovidone | SDC | + | 6.24 |
| PEOX50 | SDS | + | 2.72 |
| Poloxamer 335 | PVA | + | 2.21 |
| Poloxamer 338 | Poloxamer 407 | + | 2.76 |
| TPGS | D-mannitol | + | 2.72 |
| TPGS | Kollicoat IR | + | 2.55 |
| TPGS | Poloxamer 407 | + | 2.62 |
| TPGS | Meglumine | + | 2.74 |
| TPGS | None | + | 2.51 |
| TPGS | PAM | + | 2.32 |

PHARMACEUTICAL FORMULATION CONTAINING TADALAFIL

This application claims priority to U.S. provisional application No. 62/428,309, filed Nov. 30, 2016, U.S. provisional application No. 62/438,539, filed Dec. 23, 2016, and U.S. provisional application No. 62/502,157, filed May 5, 2017, the disclosures of which are hereby incorporated by reference as if written herein in their entireties.

FIELD OF THE INVENTION

Disclosed herein are pharmaceutical compositions with controlled particle size, increased apparent solubility and increased dissolution rate comprising as active compound Tadalafil, its salts, or derivatives thereof, which are useful in the treatment of erectile dysfunction, benign prostatic hyperplasia in combination with Finasteride or Dutasteride, pulmonary arterial hypertension and Duchenne muscular dystrophy. The pharmaceutical composition delivers earlier $t_{max}$ and faster onset of action for the treatment of erectile dysfunction. Further disclosed are methods of manufacturing the pharmaceutical formulation described herein.

BACKGROUND OF THE INVENTION

Tadalafil is a selective inhibitor of cyclic guanosine monophosphate (cGMP)-specific phosphodiesterase type 5 (PDE5). Tadalafil has the empirical formula $C_{22}H_{19}N_3O_4$ representing a molecular weight of 389.41. The structural formula is:

It is a crystalline solid that is practically insoluble in water and very slightly soluble in ethanol.

CIALIS (Tadalafil) is available as almond-shaped tablets for oral administration. Each tablet contains 2.5, 5, 10, or 20 mg of Tadalafil and the following inactive ingredients: croscarmellose sodium, hydroxypropyl cellulose, hypromellose, iron oxide, lactose monohydrate, magnesium stearate, microcrystalline cellulose, sodium lauryl sulfate, talc, titanium dioxide, and triacetin.

After single oral-dose administration, the maximum observed plasma concentration ($C_{max}$) of Tadalafil is achieved between 30 minutes and 6 hours (median time of 2 hours). Absolute bioavailability of Tadalafil following oral dosing has not been determined. The rate and extent of absorption of Tadalafil are not influenced by food; thus CIALIS may be taken with or without food.

Over a dose range of 2.5 to 20 mg, Tadalafil exposure (AUC) increases proportionally with dose in healthy subjects. Steady-state plasma concentrations are attained within 5 days of once-daily dosing, and exposure is approximately 1.6-fold greater than after a single dose. Tadalafil is eliminated predominantly by hepatic metabolism, mainly by cytochrome P450 3A4 (CYP3A4). The concomitant use of potent CYP3A4 inhibitors such as ritonavir or ketoconazole resulted in significant increases in Tadalafil AUC values.

The mean apparent volume of distribution following oral administration is approximately 63 L, indicating that Tadalafil is distributed into tissues. At therapeutic concentrations, 94% of Tadalafil in plasma is bound to proteins. Less than 0.0005% of the administered dose appeared in the semen of healthy subjects.

Tadalafil is predominantly metabolized by CYP3A4 to a catechol metabolite. The catechol metabolite undergoes extensive methylation and glucuronidation to form the methylcatechol and methylcatecholglucuronide conjugate, respectively. The major circulating metabolite is the methylcatechol glucuronide. Methylcatechol concentrations are less than 10% of glucuronide concentrations. In-vitro data suggests that metabolites are not expected to be pharmacologically active at observed metabolite concentrations.

The mean oral clearance for Tadalafil is 2.5 L/hr and the mean terminal half-life is 17.5 hours in healthy subjects. Tadalafil is excreted predominantly as metabolites, mainly in the feces (approximately 61% of the dose) and to a lesser extent in the urine (approximately 36% of the dose).

The main medical concerns surrounding Tadalafil are related to slow absorption and variable onset of action with $t_{max}$ values in the 0.5-6 hour range.

A variety of strategies have been used to attempt to overcome these issues, see for example WO 2014125343, WO2006049986, WO2012085927, WO2006091974, WO2007027612, WO2008134557, WO2012095151, WO2014092661, WO2014125352, WO2011135426, WO2016012539, WO2013109221, WO2013109223, WO2016001143, WO2014168455, WO2014202797 WO2016021975, WO2010115886 and WO2014209022.

DESCRIPTION OF THE INVENTION

Disclosed herein are pharmaceutical compositions comprising an active compound chosen from Tadalafil, its salts or derivatives thereof; and at least one primary pharmaceutical excipient chosen from polyethylene glycol glycerides composed of mono-, di- and triglycerides and mono- and diesters of polyethylene glycol (e.g.; Gelucire 44/14), polyethylene glycol (e.g; PEG2000, PEG6000), hydroxypropylcellulose (e.g; Klucell EF, Klucell LF), poloxamers (copolymers of ethylene oxide and propylene oxide blocks) (e.g; Poloxamer 407, Poloxamer 335, Poloxamer 188, Poloxamer 338), copovidone (copolymer of vinylpyrrolidone and vinyl acetate) (e.g.; Kollidon VA64), poly(2-ethyl-2-oxazoline) (e.g; PEOX50, PEOX200, PEOX500), povidone (polyvinylpyrrolidone, e.g; Plasdone K-12, PVP 40, PVP K90, PVP 10), (polyvinyl caprolactam-polyvinyl acetate-polyethylene glycol graft copolymer (e.g; Soluplus), polyoxyl 15 hydroxystearate (e.g; Solutol HS15), ethylene oxide/propylene oxide tetra functional block copolymer (e.g.; Tetronic 1107), amino methacrylate copolymer (e.g; Eudragit E PO), hydroxypropylmethylcellulose acetate succinate (e.g; HPM-CAS) and d-alpha tocopheryl polyethylene glycol 1000 succinate (TPGS); said pharmaceutical formulations characterized in that they possess at least one of the following properties:
   a) are instantaneously redispersable in physiological relevant media;
   b) are stable in solid form and in colloid solution and/or dispersion;
   c) have an apparent solubility in water of at least 0.7 mg/mL; and d) has a PAMPA permeability of at least 4×10$^{-6}$ cm/s when dispersed in Fasted State Simulated Intestinal Fluid (FaSSIF) or Fed State Simulated Intestinal Fluid (FeSSIF) biorelevant media, which does not decrease in time at least for 6 months.

In an embodiment, said pharmaceutical compositions have instantaneous redispersibility, increased apparent solubility and permeability that provide faster onset of action for the treatment of erectile dysfunction compared to the currently available formulation.

In an embodiment, said complex formulations show X-ray amorphous character in the solid form.

It has been found that only the selected combinations of primary pharmaceutical excipients and secondary pharmaceutical excipients disclosed in the present disclosure result in pharmaceutical compositions having improved physicochemical characteristics and enhanced biological performance.

The expression Tadalafil is generally used for Tadalafil, or its salts or its derivatives.

In an embodiment, said primary pharmaceutical excipient is chosen from polyethylene glycol glycerides composed of mono-, di- and triglycerides and mono- and diesters of polyethylene glycol (e.g.; Gelucire 44/14), polyethylene glycol (e.g; PEG2000, PEG6000), hydroxypropylcellulose (e.g; Klucell EF, Klucell LF), poloxamers (copolymers of ethylene oxide and propylene oxide blocks) (e.g; Poloxamer 407, Poloxamer 335, Poloxamer 188, Poloxamer 338), copovidone (copolymer of vinylpyrrolidone and vinyl acetate) (e.g.; Kollidon VA64), poly(2-ethyl-2-oxazoline) (e.g; PEOX50, PEOX200, PEOX500), povidone (polyvinylpyrrolidone, e.g; Plasdone K-12, PVP 40, PVP K90, PVP 10), (polyvinyl caprolactam-polyvinyl acetate-polyethylene glycol graft copolymer (e.g; Soluplus), polyoxyl 15 hydroxystearate (e.g; Solutol HS15), ethylene oxide/propylene oxide tetra functional block copolymer (e.g.; Tetronic 1107), amino methacrylate copolymer (e.g; Eudragit E PO), hydroxypropylmethylcellulose acetate succinate (e.g; HPMCAS) and d-alpha tocopheryl polyethylene glycol 1000 succinate (TPGS).

In an embodiment, said primary pharmaceutical excipient is chosen from hydroxypropylcellulose, poloxamers (copolymers of ethylene oxide and propylene oxide blocks), copovidone (copolymer of vinylpyrrolidone and vinyl acetate), povidone (polyvinylpyrrolidone), (polyvinyl caprolactam-polyvinyl acetate-polyethylene glycol graft copolymer, ethylene oxide/propylene oxide tetra functional block copolymer, and d-alpha tocopheryl polyethylene glycol 1000 succinate In an embodiment, said primary pharmaceutical excipient is copovidone (copolymer of vinylpyrrolidone and vinyl acetate).

In an embodiment, the composition of said copovidone (copolymer of vinylpyrrolidone (VP) and vinyl acetate (VA)) is VP:VA=60:40.

In an embodiment, said pharmaceutical composition further comprises at least one secondary pharmaceutical excipient selected from the group of sodium lauryl sulfate (SDS), dioctyl sodium sulfosuccinate (DSS), cetylpyridinium chloride (CPC), D-mannitol, sodium deoxycolate (SDC), Poloxamer 407 and meglumine.

In an embodiment, said secondary pharmaceutical excipient is dioctyl sodium sulfosuccinate or sodium lauryl sulfate.

Disclosed herein are pharmaceutical compositions comprising an active compound chosen from Tadalafil, its salts or derivatives thereof; a primary pharmaceutical excipient which is copovidone (copolymer of vinylpyrrolidone and vinyl acetate); and a secondary pharmaceutical excipient chosen from dioctyl sodium sulfosuccinate and sodium lauryl sulfate; said pharmaceutical composition characterized in that it possesses at least one of the following properties:
a) are instantaneously redispersable in physiological relevant media;
b) are stable in solid form and in colloid solution and/or dispersion;
c) have an apparent solubility in water of at least 0.7 mg/mL; and
d) has a PAMPA permeability of at least 4×10$^{-6}$ cm/s when dispersed in Fasted State Simulated Intestinal Fluid (FaSSIF) or Fed State Simulated Intestinal Fluid (FeSSIF) biorelevant media, which does not decrease in time at least for 6 months.

Figure 6:
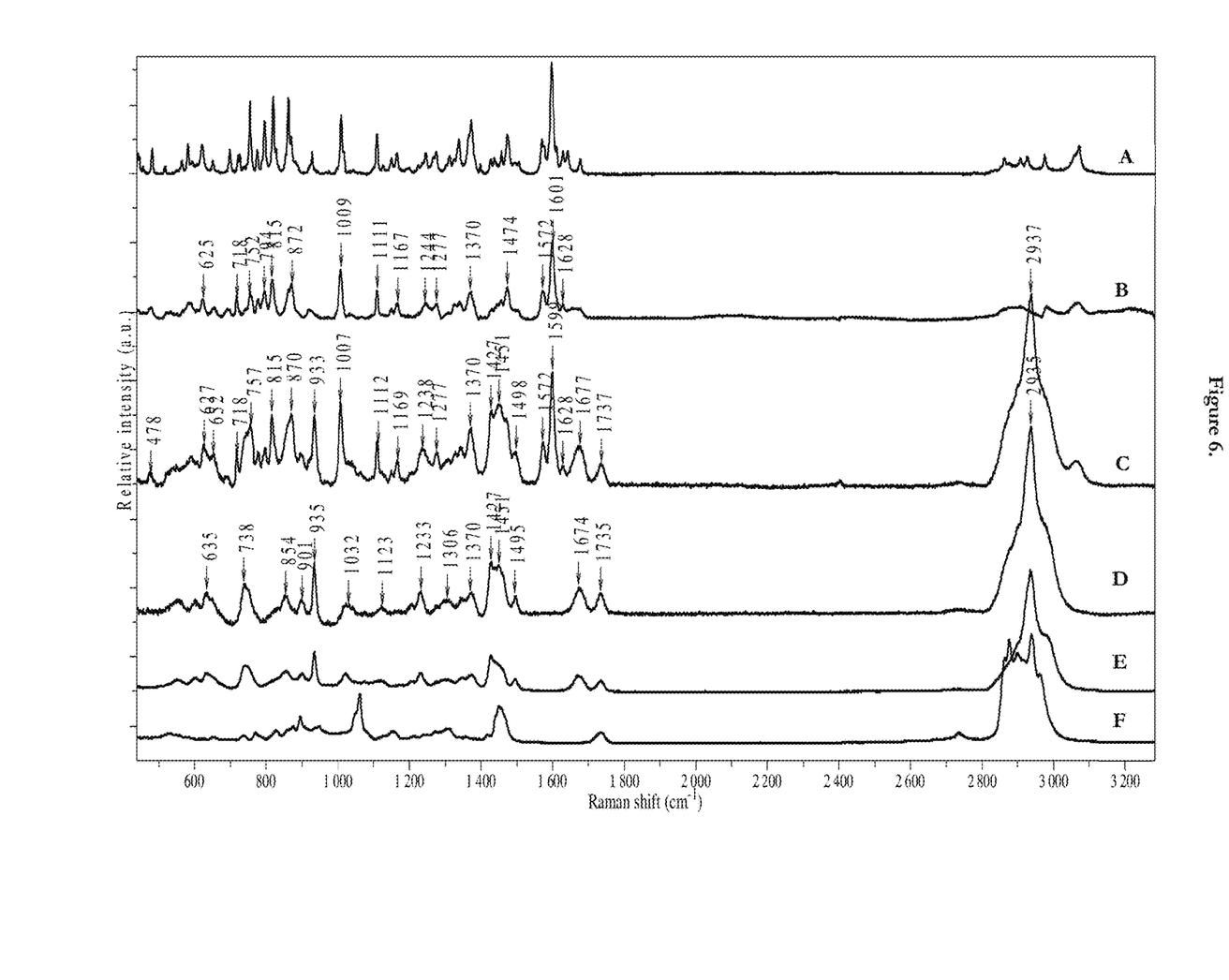
FIG. 6. shows Raman spectra of A) unformulated crystalline Tadalafil; B) Freeze dried reference Tadalafil; C) Pharmaceutical formulation of Tadalafil containing copovidone (copolymer of vinylpyrrolidone and vinyl acetate) and dioctyl sodium sulfosuccinate; D) Placebo sample containing Copovidone (copolymer of vinylpyrrolidone and vinyl acetate) and dioctyl sodium sulfosuccinate; D) Copovidone (copolymer of vinylpyrrolidone and vinyl acetate); E) Dioctyl sodium sulfosuccinate.

In an embodiment, said secondary pharmaceutical excipient is dioctyl sodium sulfosuccinate and wherein said composition is characterized by said Raman spectrum as shown in FIG. 6.

Figure 7:
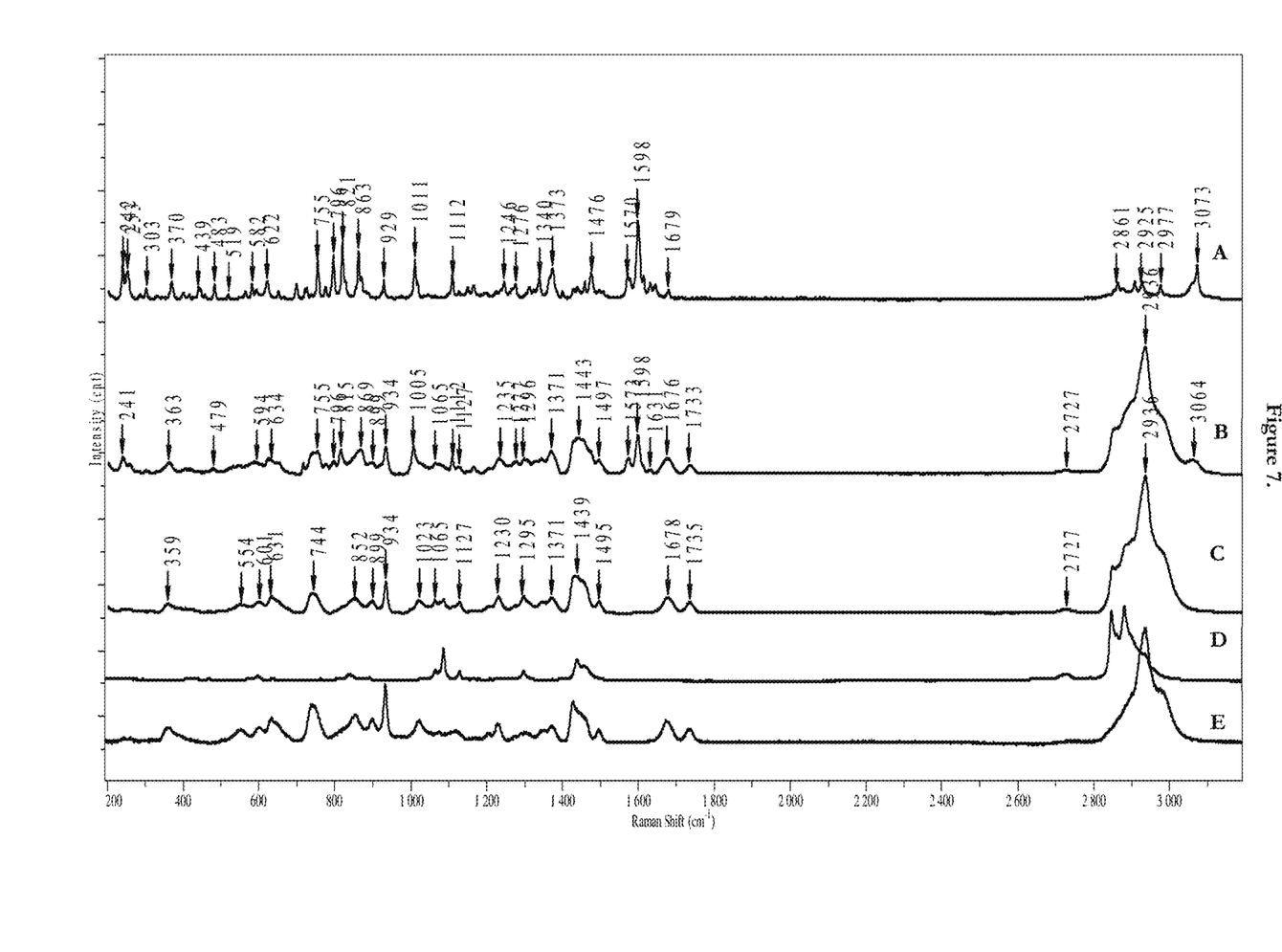
FIG. 7. shows Raman spectra of A) unformulated crystalline Tadalafil; (B) Freeze dried Tadalafil C) Pharmaceutical formulation of Tadalafil containing Copovidone (copolymer of vinylpyrrolidone and vinyl acetate) and sodium lauryl sulfate; D) Placebo sample containing Copovidone (copolymer of vinylpyrrolidone and vinyl acetate) and sodium lauryl sulfate; D) Copovidone (copolymer of vinylpyrrolidone and vinyl acetate); E) Dioctyl sodium sulfosuccinate.
Figure 8:
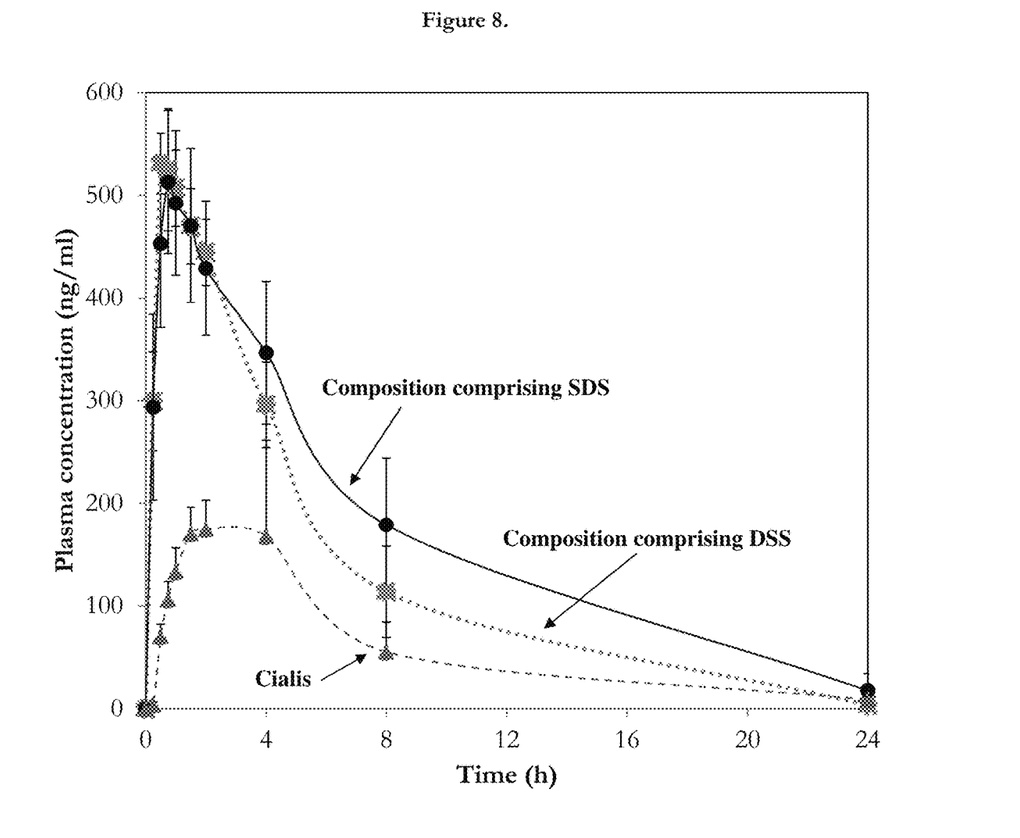
FIG. 8. shows the plasma concentrations of Tadalafil following the oral administration of 20 mg Cialis® or the pharmaceutical compositions comprising DSS and SDS to beagle dogs in the fasted state. N=3.

In an embodiment, said secondary pharmaceutical excipient is sodium lauryl sulfate and wherein said composition is characterized by said Raman spectrum as shown in FIG. 7.

In an embodiment, said pharmaceutical composition has controlled particle size in the range between 10 nm and 500 nm.

In an embodiment, said particle size is between 10 nm and 200 nm.

In an embodiment, said pharmaceutical composition has an apparent solubility in water of at least 0.7 mg/mL.

In an embodiment, said pharmaceutical composition may further comprise one or more additional active compounds.

In an embodiment, said additional active compound is chosen from agents useful for the treatment of erectile dysfunction, benign prostatic hyperplasia, pulmonary arterial hypertension and Duchenne muscular dystrophy.

In an embodiment, said pharmaceutical composition provides faster onset of action for the treatment of erectile dysfunction compared to Cialis®.

In an embodiment, said pharmaceutical composition possesses at least two of the properties described in a)-d).

In an embodiment, said pharmaceutical composition possesses at least three of the properties described in a)-d).

In an embodiment, said pharmaceutical composition has an increased dissolution rate compared to Cialis®.

Further disclosed herein is a pharmaceutical composition comprising an active compound selected from the group of Tadalafil, its salt, or derivatives thereof; at least one primary pharmaceutical excipient which is copovidone (copolymer of vinylpyrrolidone and vinyl acetate); and at least one secondary pharmaceutical excipient chosen from dioctyl sodium sulfosuccinate and sodium lauryl sulfate.

In an embodiment, the composition of said copovidone (copolymer of vinylpyrrolidone (VP)-vinyl acetate (VA)) is VP:VA=60:40.

In an embodiment, said pharmaceutical composition comprises a primary pharmaceutical excipient which is a copovidone (copolymer of vinylpyrrolidone and vinyl acetate) and a secondary pharmaceutical excipient which is dioctyl sodium sulfosuccinate or sodium lauryl sulfate, in a total amount ranging from about 1.0 weight % to about 95.0 weight % based on the total weight of the pharmaceutical composition.

In an embodiment, said pharmaceutical composition comprises a primary pharmaceutical excipient which is a copovidone (copolymer of vinylpyrrolidone and vinyl acetate) and a secondary pharmaceutical excipient which is dioctyl sodium sulfosuccinate or sodium lauryl sulfate, in a total amount ranging from about 50.0 weight % to about 95.0 weight % based on the total weight of the pharmaceutical composition.

Further disclosed herein is a process for the preparation of said pharmaceutical composition, comprising the steps of dissolving Tadalafil, its salt, or derivatives thereof, and at least one primary pharmaceutical excipient chosen from polyethylene glycol glycerides composed of mono-, di- and triglycerides and mono- and diesters of polyethylene glycol (e.g.; Gelucire 44/14), polyethylene glycol (e.g; PEG2000, PEG6000), hydroxypropylcellulose (e.g; Klucell EF, Klucell LF), poloxamers (copolymers of ethylene oxide and propylene oxide blocks) (e.g; Poloxamer 407, Poloxamer 335, Poloxamer 188, Poloxamer 338), copovidone (copolymer of vinylpyrrolidone and vinyl acetate) (e.g.; Kollidon VA64), poly(2-ethyl-2-oxazoline) (e.g; PEOX50, PEOX200, PEOX500), povidone (polyvinylpyrrolidone, e.g; Plasdone K-12, PVP 40, PVP K90, PVP 10), (polyvinyl caprolactam-polyvinyl acetate-polyethylene glycol graft copolymer (e.g; Soluplus), polyoxyl 15 hydroxystearate (e.g; Solutol HS15), ethylene oxide/propylene oxide tetra functional block copolymer (e.g.; Tetronic 1107), amino methacrylate copolymer (e.g; Eudragit E PO), hydroxypropylmethylcellulose acetate succinate (e.g; HPMCAS) and d-alpha tocopheryl polyethylene glycol 1000 succinate (TPGS) in a pharmaceutically acceptable solvent, and mixing with an aqueous solution containing optionally least one secondary pharmaceutical excipient selected from the group of sodium lauryl sulfate (SDS), dioctyl sodium sulfosuccinate (DSS), cetylpyridinium chloride (CPC), D-Mannitol, sodium deoxycolate (SDC), Poloxamer 407 and meglumine in a pharmaceutically acceptable solvent mixture.

In an embodiment, said primary pharmaceutical excipient is copovidone (copolymer of vinylpyrrolidone and vinyl acetate).

In an embodiment, said secondary pharmaceutical excipient is sodium lauryl sulfate (SDS) or dioctyl sodium sulfosuccinate (DSS).

In an embodiment, said pharmaceutically acceptable solution of Tadalafil, its salts or derivatives and at least one primary pharmaceutical excipient is prepared using a pharmaceutically acceptable solvent chosen from methanol, ethanol, 1-propanol, 2-propanol, acetone, acetonitrile, dimethyl-sulfoxide, tetrahydrofuran, methyl-ethyl ketone or combinations thereof.

In an embodiment, said pharmaceutically acceptable solvent mixture is a solvent mixture of a pharmaceutically acceptable solvent chosen from methanol, ethanol, 1-propanol, 2-propanol, acetone, acetonitrile, dimethyl-sulfoxide, tetrahydrofuran, methyl-ethyl ketone or combinations thereof and water.

In an embodiment, said pharmaceutically acceptable solvent is tetrahydrofuran.

In an embodiment, said pharmaceutically acceptable solution and said aqueous solution are miscible with each other.

In an embodiment, said pharmaceutically acceptable solvent is miscible with water.

In an embodiment, said aqueous solution comprises 0.1 to 99.9% weight of the final solution.

In an embodiment, said aqueous solution comprises 50 to 90% weight of the final solution.

In an embodiment, said aqueous solution comprises 50 to 80% weight of the final solution.

In an embodiment, said aqueous solution comprises 50 to 70% weight of the final solution.

In an embodiment, said aqueous solution comprises 50 to 60% weight of the final solution.

In an embodiment, said aqueous solution comprises 45 to 55% weight of the final solution.

In an embodiment, said aqueous solution comprises 50% weight of the final solution.

In an embodiment, said aqueous solution comprises 5 to 45% weight of the final solution.

In an embodiment, said aqueous solution comprises 5 to 35% weight of the final solution.

In an embodiment, said aqueous solution comprises 5 to 25% weight of the final solution.

In an embodiment, said pharmaceutically acceptable solvent comprises 0.1 to 99.9% weight of the pharmaceutically acceptable solvent mixture.

In an embodiment, said pharmaceutically acceptable solvent comprises 50 to 90% weight of the pharmaceutically acceptable solvent mixture.

In an embodiment, said pharmaceutically acceptable solvent comprises 50 to 80% weight of the pharmaceutically acceptable solvent mixture.

In an embodiment, said pharmaceutically acceptable solvent comprises 50 to 70% weight of the pharmaceutically acceptable solvent mixture.

In an embodiment, said pharmaceutically acceptable solvent comprises 50 to 60% weight of the pharmaceutically acceptable solvent mixture.

In an embodiment, said pharmaceutically acceptable solvent comprises 45 to 55% weight of the pharmaceutically acceptable solvent mixture.

In an embodiment, said pharmaceutically acceptable solvent comprises 50% weight of the pharmaceutically acceptable solvent mixture.

In an embodiment, said pharmaceutically acceptable solvent comprises 5 to 45% weight of the pharmaceutically acceptable solvent mixture.

In an embodiment, said pharmaceutically acceptable solvent comprises 5 to 35% weight of the pharmaceutically acceptable solvent mixture.

In an embodiment, said pharmaceutically acceptable solvent comprises 5 to 25% weight of the pharmaceutically acceptable solvent mixture.

In an embodiment, said pharmaceutical composition may comprise additional pharmaceutically acceptable excipients.

In an embodiment, said pharmaceutical composition is suitable for oral, pulmonary, rectal, colonic, parenteral, intracisternal, intravaginal, intraperitoneal, ocular, otic, local, buccal, nasal, or topical administration.

In an embodiment, said pharmaceutical composition is suitable for oral administration.

In an embodiment, said pharmaceutical composition is for use of manufacture of a medicament for the treatment of erectile dysfunction, benign prostatic hyperplasia, pulmonary arterial hypertension and Duchenne muscular dystrophy.

In an embodiment, said pharmaceutical composition is used for the treatment of erectile dysfunction, benign prostatic hyperplasia, pulmonary arterial hypertension and Duchenne muscular dystrophy.

Disclosed herein is a method of treatment of erectile dysfunction, benign prostatic hyperplasia, pulmonary arterial hypertension and Duchenne muscular dystrophy comprising the administration of a therapeutically effective amount of a pharmaceutical composition as described herein.

In an embodiment, a method for reducing the therapeutically effective dosage of Tadalafil compared to commercially available Cialis comprises the oral administration of a pharmaceutical composition as described herein.

Further disclosed herein is a stable pharmaceutical composition comprising
a. 10-40% by weight of Tadalafil, its salt, or derivatives thereof;
b. 35-70% by weight of a copovidone (copolymer of vinylpyrrolidone and vinyl acetate); and
c. 5-50% by weight of dioctyl sodium sulfosuccinate or sodium lauryl sulfate
wherein said pharmaceutical formulation has a controlled particle size in the range between 10 nm and 500 nm; and wherein said pharmaceutical composition cannot be prepared via a milling process, high pressure homogenization process or encapsulation process.

In an embodiment, said particle size is between 10 nm and 200 nm.

In an embodiment, said pharmaceutical composition shows significantly improved exposure, earlier $t_{max}$, and higher $C_{max}$ compared to Cialis® which will allow the reduction of the dose and provide faster onset of action.

In an embodiment, said pharmaceutical composition has a faster onset of action compared to Cialis®.

In an embodiment, said pharmaceutical composition is instantaneously redispersable in physiological relevant media.

In an embodiment, said pharmaceutical composition is stable in solid form and in colloid solution and/or dispersion.

In an embodiment, said pharmaceutical composition has apparent solubility in water of at least 0.7 mg/mL.

In an embodiment, Tadalafil shows X-ray amorphous characters in said pharmaceutical composition.

In an embodiment, said pharmaceutical composition has a PAMPA permeability of at least $4 \times 10^{-6}$ cm/s when dispersed in water, FaSSIF or FeSSIF biorelevant media, which does not decrease in time at least for 6 months.

In an embodiment, said pharmaceutical composition containing copovidone (copolymer of vinylpyrrolidone and vinyl acetate) and dioctyl sodium sulfosuccinate is characterized by the Raman spectrum shown in FIG. 6.

In an embodiment, said pharmaceutical composition containing copovidone (copolymer of vinylpyrrolidone and vinyl acetate) and sodium lauryl sulfate is characterized by the Raman spectra as shown in FIG. 7.

In some embodiments, said pharmaceutical composition may additionally include one or more pharmaceutical excipients, auxiliary materials, carriers, active agents or combinations thereof.

In some embodiments, active compounds may include active compound useful for the treatment of erectile dysfunction, benign prostatic hyperplasia, pulmonary arterial hypertension and Duchenne muscular dystrophy.

In some embodiment, the complex structure of the pharmaceutical composition is different from the core-shell type milled particle, precipitated encapsulated particles and micelles.

The pharmaceutical composition can be formulated: (a) for administration selected from the group consisting of oral, pulmonary, rectal, colonic, parenteral, intracisternal, intravaginal, intraperitoneal, ocular, otic, local, buccal, nasal, and topical administration; (b) into a dosage form selected from the group consisting of liquid dispersions, gels, aerosols, ointments, creams, lyophilized formulations, sachets, tablets, capsules; (c) into a dosage form selected from the group consisting of fast release formulations, controlled release formulations, fast melt formulations, delayed release formulations, extended release formulations, pulsatile release formulations, and mixed immediate release and controlled release formulations; or (d) any combination of (a), (b), and (c).

The pharmaceutical composition can be formulated by adding different types of pharmaceutical excipients for oral administration in solid, liquid; local (powders, ointments or drops); or topical administration, and the like.

In an embodiment, the pharmaceutical dosage form is a solid dosage form, although any pharmaceutically acceptable dosage form can be utilized.

Solid dosage forms for oral administration include, but are not limited to, capsules, tablets, pills, powders (sachets), and granules. In such solid dosage forms, the pharmaceutical formulation is admixed with at least one of the following: one or more inert excipients (or carriers):

(a) fillers or extenders, such as, lactose, sucrose, glucose, mannitol, sorbitol, dextrose, dextrates, dextrin, erythritol, fructose, isomalt, lactitol, maltitol, maltose, maltodextrin, trehalose, xylitol, starches, microcrystalline cellulose, dicalcium phosphate, calcium carbonate, magnesium carbonate, magnesium oxide;

(b) sweetening, flavoring, and perfuming agents such as saccharin, saccharin sodium, acesulfame potassium, alitame, aspartame, glycine, inulin, neohesperidin dihydrochalcone, neotame, sodium cyclamate, sucralose, tagatose, thaumatin, citric acid, adipic acid, fumaric acid, leucine, malic acid, menthol, propionic acid, tartaric acid;

(c) binders, such as cellulose derivatives, acrylic acid derivatives, alginates, gelatin, polyvinylpyrrolidone, starch derivatives, dextrose, dextrates, dextrin, maltose, maltodextrin; (d) disintegrating agents, such as crospovidon, effervescent compositions, croscarmellose sodium and other cellulose derivatives, sodium starch glycolate and other starch derivatives, alginic acid, certain pharmaceutical silicates and sodium carbonate;

(e) solution retarders, such as acrylates, cellulose derivatives, paraffin; (f) absorption accelerators, such as quaternary ammonium compounds; (g) wetting agents, such as polysorbates, cetyl alcohol and glycerol monostearate;

(h) lubricants such as talc, stearic acid and its derivatives, solid polyethylene glycols, sodium lauryl sulfate, glyceryl behenate, medium-chain triglycerides or mixtures thereof. For capsules, tablets, sachets and pills, the dosage forms may also comprise buffering agents.

In an embodiment, the dosage form of the invention is liquid dispersible granules, sachets, liquid dispersible tablets, orodispersible tablets, orally dissolving tablets, chewing tablets and immediate release (IR) tablets.

In an embodiment, said liquid dispersible granule, sachet, liquid dispersible tablets, orodispersible tablet, orally dissolving tablet, chewing tablets and immediate release tablets comprise the pharmaceutical formulation of the present invention together with pharmaceutically acceptable excipients selected from the group of fillers or extenders, such as, lactose, sucrose, glucose, mannitol, sorbitol, dextrose, dextrates, dextrin, erythritol, fructose, isomalt, lactitol, maltitol, maltose, maltodextrin, trehalose, xylitol, starches, microcrystalline cellulose, dicalcium phosphate, calcium carbonate, magnesium carbonate, magnesium oxide.

In an embodiment, said liquid dispersible granules, sachets, liquid dispersible tablets, orodispersible tablets, orally dissolving tablets, chewing tablets and immediate release (IR) tablets comprise the pharmaceutical formulation of the present invention together with pharmaceutically acceptable excipients selected from the group of sweetening, flavoring, and perfuming agents such as saccharin, saccharin sodium, acesulfame potassium, alitame, aspartame, glycine, inulin, neohesperidin dihydrochalcone, neotame, sodium cyclamate, sucralose, tagatose, thaumatin, citric acid, adipic acid, fumaric acid, leucine, malic acid, menthol, propionic acid, tartaric acid.

Further disclosed herein is liquid dispersible granules, sachets, liquid dispersible tablets, orodispersible tablets, orally dissolving tablets, chewing tablets and immediate release tablets comprising
- a. 25-95% stable pharmaceutical formulation of the present invention;
- b. 5-75% fillers or extenders;
- c. 0.5-25% binders;
- d. 0.1-5% sweetening, flavoring, and perfuming agents;

wherein said liquid dispersible granules, sachets, liquid dispersible tablets, orodispersible tablets, orally dissolving tablets, chewing tablets and immediate release tablets disperse within 10 min in liquid or biorelevant media or gastric acid.

In an embodiment, said dispersion time is between 0.1 min and 10 min.

In an embodiment, said dispersion time is between 0.1 min and 5 min.

In an embodiment, said dispersion time is between 0.1 min and 3 min.

In an embodiment, said dispersion time is between 0.1 min and 1 min.

In an embodiment, Hausner-ratio of the said dosage forms of the pharmaceutical formulations of the present invention is less than 1.25.

In an embodiment, Hausner-ratio of the said dosage forms of the pharmaceutical formulations of the present invention is between 1.00 and 1.11.

In an embodiment, the particle size (D(90)) of said granules of the pharmaceutical formulations is less than 2000 micrometers.

In an embodiment, 60-80% of the said granules of the pharmaceutical formulations are in the size range under 800 micrometers.

In an embodiment, said liquid is water, saliva, other physiologically or biologically acceptable fluid or liquid.

In an embodiment, the dosage form of the invention is liquid dispersible granules, sachets, liquid dispersible tablets, orodispersible tablets, orally dissolving tablets, chewing tablets and immediate release tablets.

In an embodiment, said liquid dispersible granules, sachets, liquid dispersible tablets, orodispersible tablets, orally dissolving tablets, chewing tablets and immediate release tablets comprise the pharmaceutical formulation of the present invention together with pharmaceutically acceptable excipients selected from the group of fillers or extenders, such as, lactose, sucrose, glucose, mannitol, sorbitol, dextrose, dextrates, dextrin, erythritol, fructose, isomalt, lactitol, maltitol, maltose, maltodextrin, trehalose, xylitol, calcium carbonate, calcium lactate, calcium phosphate, calcium silicate, calcium sulfate, powdered cellulose, microcrystalline cellulose, silicified microcrystalline cellulose, corn starch, pregelatinized corn starch, fumaric acid, magnesium carbonate, magnesium oxide, polymethacrilates, sodium chloride, talc, aluminium oxide, magnesium-aluminium silicate, colloidal silicon dioxide.

In an embodiment, said liquid dispersible granules, sachets, liquid dispersible tablets, orodispersible tablets, orally dissolving tablets, chewing tablets and immediate release tablets comprise the pharmaceutical formulation of the present invention together with pharmaceutically acceptable excipients selected from the group of dissolution modifiers, such as, carboxymethylcellulose sodium, hypromellose, hypromellose acetyl succinate, crospovidone, cyclodextrins, agar, alginic acid, carbomers, carnauba wax, carrageenan, guar gum, hydroxypropyl cellulose, hypromellose phthalate, methylcellulose, polacrilin potassium, polyethylene oxide, polyoxylglycerides, polyvinyl alcohol, sodium acetate, sodium alginate, sodium hyaluronate, xanthan gum, polycarbophil, cetyl alcohol, chitosan.

In an embodiment, said liquid dispersible granules, sachets, liquid dispersible tablets, orodispersible tablets, orally dissolving tablets, chewing tablets and immediate release tablets comprise the pharmaceutical formulation the present invention together with pharmaceutically acceptable excipients selected from the group of sweetening, flavoring, and perfuming agents such as saccharin, saccharin sodium, acesulfame potassium, alitame, aspartame, glycine, inulin, neohesperidin dihydrochalcone, neotame, sodium cyclamate, sucralose, tagatose, thaumatin, citric acid, adipic acid, fumaric acid, leucine, malic acid, menthol, propionic acid, tartaric acid.

Further disclosed herein is liquid dispersible granules, sachets, liquid dispersible tablets, orodispersible tablets, orally dissolving tablets, chewing tablets and immediate release tablets comprising
- a. 25-95% stable pharmaceutical formulation of the present invention;
- b. 0.5-75% fillers or extenders such as lactose, sucrose, glucose, mannitol, sorbitol, dextrose, dextrates, dextrin, erythritol, fructose, isomalt, lactitol, maltitol, maltose, maltodextrin, trehalose, xylitol, lactose, sucrose, glucose, mannitol, sorbitol, dextrose, dextrates, dextrin, erythritol, fructose, isomalt, lactitol, maltitol, maltose, maltodextrin, trehalose, xylitol, calcium carbonate, calcium lactate, calcium phosphate, calcium silicate, calcium sulfate, powdered cellulose, microcrystalline cellulose, silicified microcrystalline cellulose, corn starch, pregelatinized corn starch, fumaric acid, magnesium carbonate, magnesium oxide, polymethacrilates, sodium chloride, talc, aluminium oxide, magnesium-aluminium silicate, colloidal silicon dioxide;
- c. 0.5-25% dissolution modifiers such as carboxymethylcellulose sodium, hypromellose, hypromellose acetyl succinate, crospovidone, cyclodextrins, agar, alginic acid, carbomers, carnauba wax, carrageenan, guar gum, hydroxypropyl cellulose, hypromellose phthalate, methylcellulose, polacrilin potassium, polyethylene oxide, polyoxylglycerides, polyvinyl alcohol, sodium acetate, sodium alginate, sodium hyaluronate, xanthan gum, polycarbophil, cetyl alcohol, chitosan;
- d. 0.1-5% sweetening, flavoring, and perfuming agents such as saccharin, saccharin sodium, acesulfame potassium, alitame, aspartame, glycine, inulin, neohesperidin dihydrochalcone, neotame, sodium cyclamate, sucralose, tagatose, thaumatin, citric acid, adipic acid, fumaric acid, leucine, malic acid, menthol, propionic acid, tartaric acid;
- e. 0.1-1% lubricants;
- f. 0.1-15% docusate sodium, sodium dodecyl sulfate, ammonium lauryl ether sulfate, benzalkonium chloride, benzethonium chloride, cetyl trimethylammonium bromide, polyoxyethelene alkylphenylethersm poloxamers, polyoxyethelene fatty acid glycerides, sorbitan esters;

wherein said liquid dispersible granules, sachets, liquid dispersible tablets, orodispersible tablets, orally dissolving tablets, chewing tablets and immediate release tablets disperse within 10 min.

In an embodiment, said dispersion time is between 0.1 min and 3 min.

In an embodiment, said dispersion time is between 0.1 min and 1 min.

In an embodiment, the dosage form is chosen from liquid dispersible granules, sachets, liquid dispersible tablets, orodispersible tablets, orally dissolving tablets, chewing tablets and immediate release tablets.

Advantages of the Tadalafil pharmaceutical composition of the present disclosure include, but are not limited to (1) physical and chemical stability, (2) instantaneous redispersibility, (3) stability in colloid solution or dispersion in the therapeutic time window, (4) increased apparent solubility and permeability compared to the conventional Tadalafil formulation, (5) decreased time to onset of action for the treatment of erectile dysfunction and (6) good processability.

In an embodiment, the Tadalafil pharmaceutical composition has an enhanced pharmacokinetic performance. The pharmaceutical Tadalafil composition shows decreased $t_{max}$ and time to onset of action when compared to the commercially available formulations of Tadalafil.

BRIEF DESCRIPTION OF THE DRAWINGS

The accompanying figures, which are incorporated and form part of the specification, merely illustrate certain embodiments and should not be construed as limiting. They are meant to serve to explain specific modes to those skilled in the art.

EXAMPLES

Specific, non-limiting embodiments will further be demonstrated by the following examples.

Figure 1:
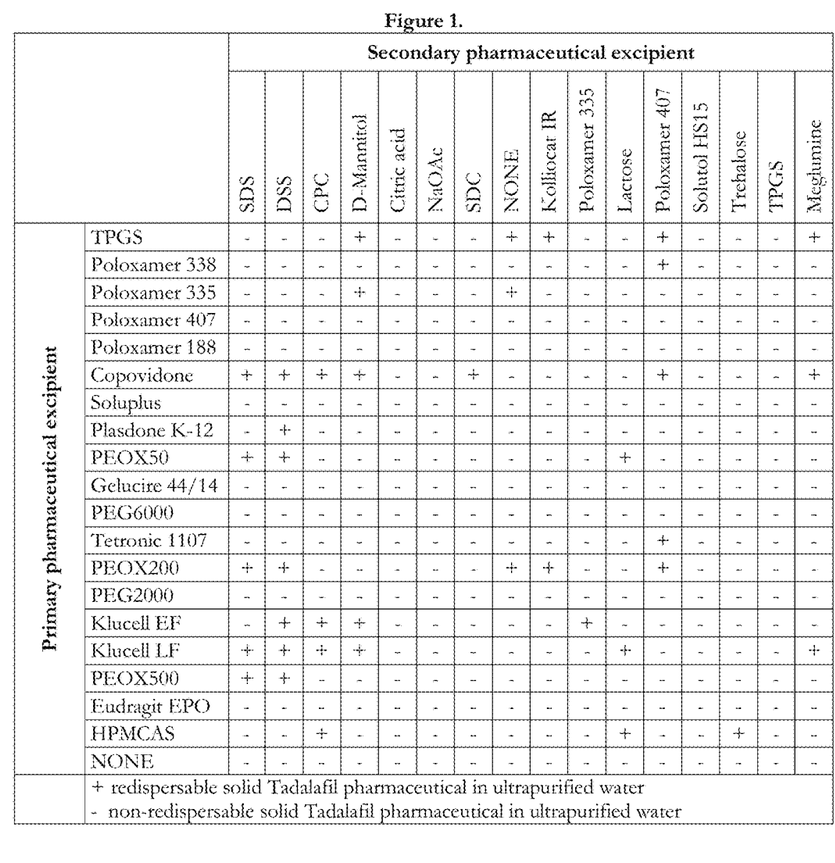
FIG. 1. shows the redispersibility of Tadalafil pharmaceutical formulations in ultrapurified water.

Selection of Tadalafil Pharmaceutical Composition with Improved Material Properties Several primary and secondary pharmaceutical excipients and their combinations were tested to determine compositions having instantaneous redispersibility as shown in FIG. 1.

Examples that displayed an acceptable level of redispersibility was selected for further analysis.

Figure 2:
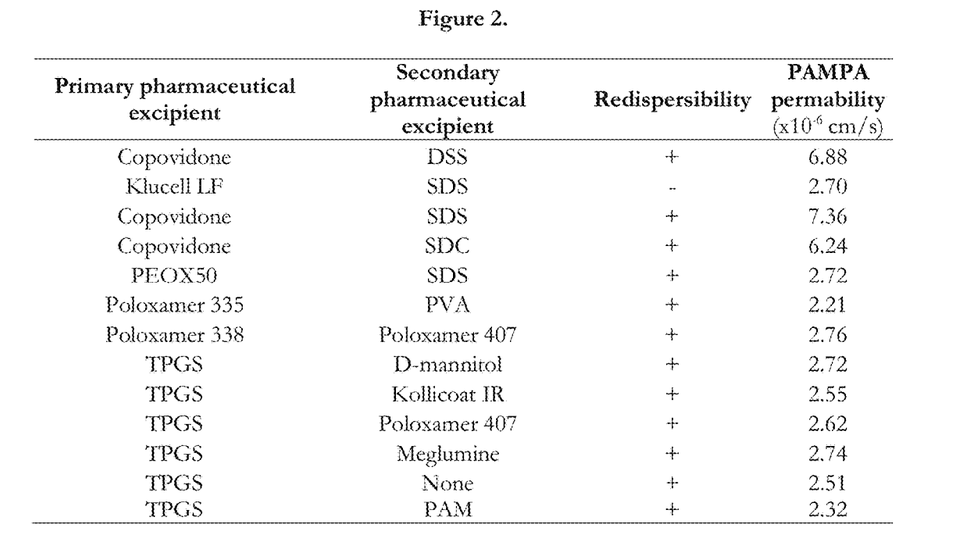
FIG. 2. shows the PAMPA permeability and redispersibility of selected pharmaceutical Tadalafil formulations.

PAMPA permeability of the selected compositions was measured in order to select the pharmaceutical Tadalafil compositions having the best in-vitro performance (FIG. 2). PAMPA permeability measurements were performed as described by M. Kansi et al. (Journal of medicinal chemistry, 41, (1998) pp 1007) with modifications based on S. Bendels et al (Pharmaceutical research, 23 (2006) pp 2525). Permeability was measured in a 96-well plate assay across an artificial membrane composed of dodecane with 20% soy lecithin supported by a PVDF membrane (Millipore, USA). The receiver compartment was phosphate buffered saline (pH 7.0) supplemented with 1% sodium dodecyl sulfate. The assay was performed at room temperature; incubation time was 4 hours in ultrapurified water or 10-20 and 30 minutes in simulates saliva, respectively. The concentration in the receiver compartment was determined by UV-VIS spectrophotometry (Thermo Scientific Genesys S10).

Copovidone (copolymer of vinylpyrrolidone and vinyl acetate); and dioctyl sodium sulfosuccinate and sodium lauryl sulfate were selected as primary and secondary pharmaceutical excipients, respectively, to prepare Tadalafil pharmaceutical compositions having improved material characteristics.

High Performing Compositions of Tadalafil

Solid Tadalafil pharmaceutical compositions were prepared by using different ratios of primary and secondary pharmaceutical excipients. The ratio of the primary and secondary pharmaceutical excipients did not have effect on the PAMPA permeability of the pharmaceutical compositions prepared. Tadalafil pharmaceutical composition comprising Tadalafil:copovidone (copolymer of vinylpyrrolidone and vinyl acetate):dioctyl sodium sulfosuccinate with the weight ratio of 1:3:0.5 was selected for further work. A second Tadalafil pharmaceutical composition comprising Tadalafil:copovidone (copolymer of vinylpyrrolidone and vinyl acetate):sodium lauryl sulfate with the weight ratio of 1:4:1 was also selected for further work.

Manufacturing of Tadalafil Pharmaceutical Composition

A solution mixture of Tadalafil pharmaceutical composition was prepared by mixing process. A solution 1 containing 1-10 mg/mL Tadalafil and 3-30 mg/mL copovidone (copolymer of vinylpyrrolidone and vinyl acetate) in Tetrahydrofuran was mixed with aqueous Solution 2 containing 0.125-1.5 mg/mL dioctyl sodium sulfosuccinate in different ratios. The resulting solution mixture of the Tadalafil pharmaceutical formulation was produced at atmospheric pressure and ambient temperature. The resulting solution mixture was frozen on acetone-dry-ice mixture and then it was lyophilized using a freeze drier equipped with −110° C. ice condenser, with a vacuum pump.

A solution of Tadalafil pharmaceutical composition was also prepared dissolving 10-60 mg/mL Tadalafil, 40-240 mg/mL copovidone (copolymer of vinylpyrrolidone and vinyl acetate) and 10-60 mg/mL sodium lauryl sulfate in Tetrahydrofuran:water=2:1 solution mixture. The resulting solution was prepared at atmospheric pressure and ambient temperature, and then fed into a spray-dryer.

Different concentrations and solvent ratios were tested to determine the highest performing manufacturing conditions.

Based on the results, 5 mg/mL Tadalafil, 15 mg/mL copovidone (copolymer of vinylpyrrolidone and vinyl acetate) and 0.625 mg/mL dioctyl sodium sulfosuccinate were chosen for starting concentrations. The highest performing ratio of the solutions was found to be at 1:4. The spray-dried pharmaceutical formulation was used for iv-vivo dog PK studies.

Based on the results, 5 mg/mL Tadalafil, 15 mg/mL copovidone (copolymer of vinylpyrrolidone and vinyl acetate) and 1.25 mg/mL sodium lauryl sulfate were chosen for starting concentrations. The highest performing ratio of the solutions was found to be at 1:2.

Based on the results, 17 mg/mL Tadalafil, 62 mg/mL copovidone (copolymer of vinylpyrrolidone and vinyl acetate) and 17 mg/mL sodium lauryl sulfate were chosen for starting concentrations. The solvent mixture was Tetrahydrofuran:water=2:1. The spray-dried pharmaceutical composition was used for in-vivo dog PK studies.

Solution mixtures of the highest performing Tadalafil pharmaceutical formulations were spray-dried (Yamato DL-410/GAS410) in order to obtain solid powder. The production parameters used are as follows: $T_{inlet}$=95° C., Drying airflow=0.8 m³/min, Solution feed rate=18 mL/min, atomization pressure=1 bar, $T_{out}$=63-64° C.

Improved Apparent Solubility of Tadalafil Pharmaceutical Composition

The apparent solubility of Tadalafil pharmaceutical compositions was measured by UV-VIS spectroscopy at room temperature. The solid Tadalafil pharmaceutical compositions were dispersed in ultrapurified in 0.1-0.5 mg/mL Tadalafil equivalent concentration range. The resulting solutions were filtered by 100 nm disposable syringe filter. The Tadalafil content of the filtrate was measured by UV-Vis spectrophotometry and the apparent solubility was calculated. The filtrate may contain the particles of the Tadalafil pharmaceutical composition which could not be filtrated out using 100 nm pore size filter.

The apparent solubility of Tadalafil pharmaceutical composition was 0.7 mg/mL, when 1 mg/mL Tadalafil equivalent compositions were dispersed in ultrapurified water, respectively.

Apparent solubility of Tadalafil pharmaceutical composition was at least 0.7 mg/mL.

Improved Dissolution Profile of Tadalafil Pharmaceutical Composition

Figure 3:
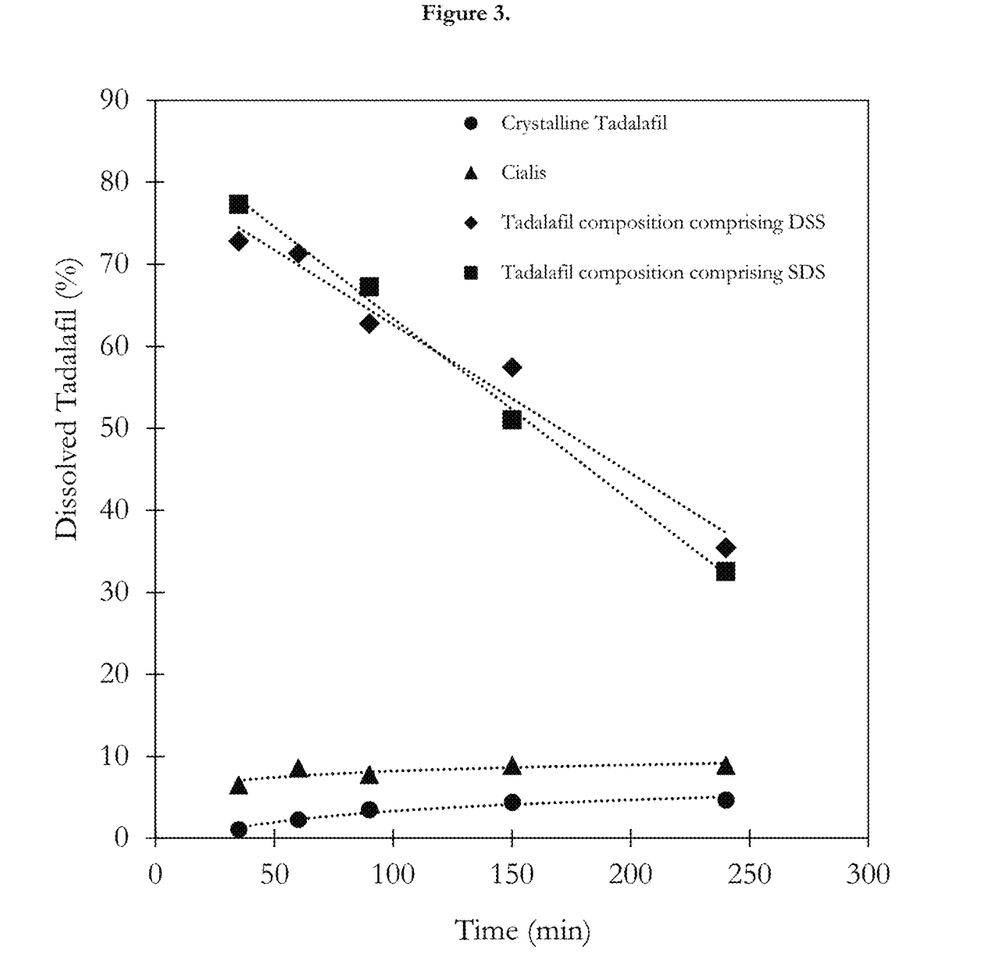
FIG. 3. shows the dissolution of unformulated, crystalline Tadalafil, Cialis®, Tadalafil composition comprising DSS and Tadalafil composition comprising SDS.

Comparative dissolution tests were performed on the Tadalafil pharmaceutical compositions, the unformulated crystalline Tadalafil and Cialis® (commercial formulation). The samples were dispersed in purified water at 0.2 mg/mL concentrations. After 30 minutes simulated gastric fluid was added to the systems. After further 30 minutes the pH was neutralized with sodium maleate base and FaSSIF solution was added. The dissolved amount was measured with UV-VIS spectrophotometry after filtration with 0.1 μm pore size filter at different time points. The dissolution of Tadalafil did not exceed 10% from crystalline Tadalafil or Cialis®. It was above 60% for the pharmaceutical formulations over two hours (FIG. 3).

Comparative In-Vitro PAMPA Assays

PAMPA permeabilities of Tadalafil pharmaceutical compositions in water ($H_2O$), FaSSIF (Fa) and FeSSIF (Fe) media were above $7.6 \times 10^{-6}$ cm/s, $7.2 \times 10^{-6}$ cm/s and $4.3 \times 10^{-6}$ cm/s, respectively, while it was $0.6 \times 10^{-6}$ cm/s, $0.6 \times 10^{-6}$ cm/s and $0.8 \times 10^{-6}$ cm/s in water, FaSSIF and FeSSIF media for the unformulated, crystalline reference. PAMPA permeability of Cialis® in water, FaSSIF and FeSSIF media was above $0.9 \times 10^{-6}$ cm/s, $0.8 \times 10^{-6}$ cm/s and $1.1 \times 10^{-6}$ cm/s, respectively.

TABLE 1 shows PAMPA permeabilities of different pharmaceutical formulations comprising Tadalafil.

| | PAMPA permeability ($\times 10^{-6}$ cm/s) | | |
|---|---|---|---|
| | Water | FaSSIF | FeSSIF |
| Unformulated, crystalline Tadalafil | 0.6 | 0.6 | 0.8 |
| Cialis ® | 0.9 | 0.8 | 1.1 |
| Tadalafil pharmaceutical composition comprising DSS | 7.7 | 7.2 | 5.3 |
| Tadalafil pharmaceutical composition comprising SDS | 8.9 | 8.7 | 7.0 |

Stability of the Solid Form

PAMPA permeability of the solid Tadalafil pharmaceutical compositions was used to monitor the physical stability of the pharmaceutical formulation. PAMPA permeability was measured after storage at different conditions. 2 months and 6 months storage at 40° C., 75% relative humidity for the composition comprising DSS and SDS, respectively, showed no significant decrease in the measured PAMPA permeability under any of the conditions tested, see Table 2.

TABLE 2

| | Storage condition | PAMPA permeability ($\times 10^{-6}$ cm/s) | | |
|---|---|---|---|---|
| | | Water | FaSSIF | FeSSIF |
| Tadalafil pharmaceutical composition comprising DSS | After 1 month at 40° C. | 7.4 | 6.8 | 7.2 |
| Tadalafil pharmaceutical composition comprising DSS | After 2 months at 40° C. | 7.8 | 7.1 | 4.2 |
| Tadalafil pharmaceutical composition comprising SDS | After 3 months at 40° C. | 7.6 | 6.7 | 5.7 |
| Tadalafil pharmaceutical composition comprising SDS | After 6 months at 40° C. | 7.2 | 6.6 | 5.4 |

Figure 4:
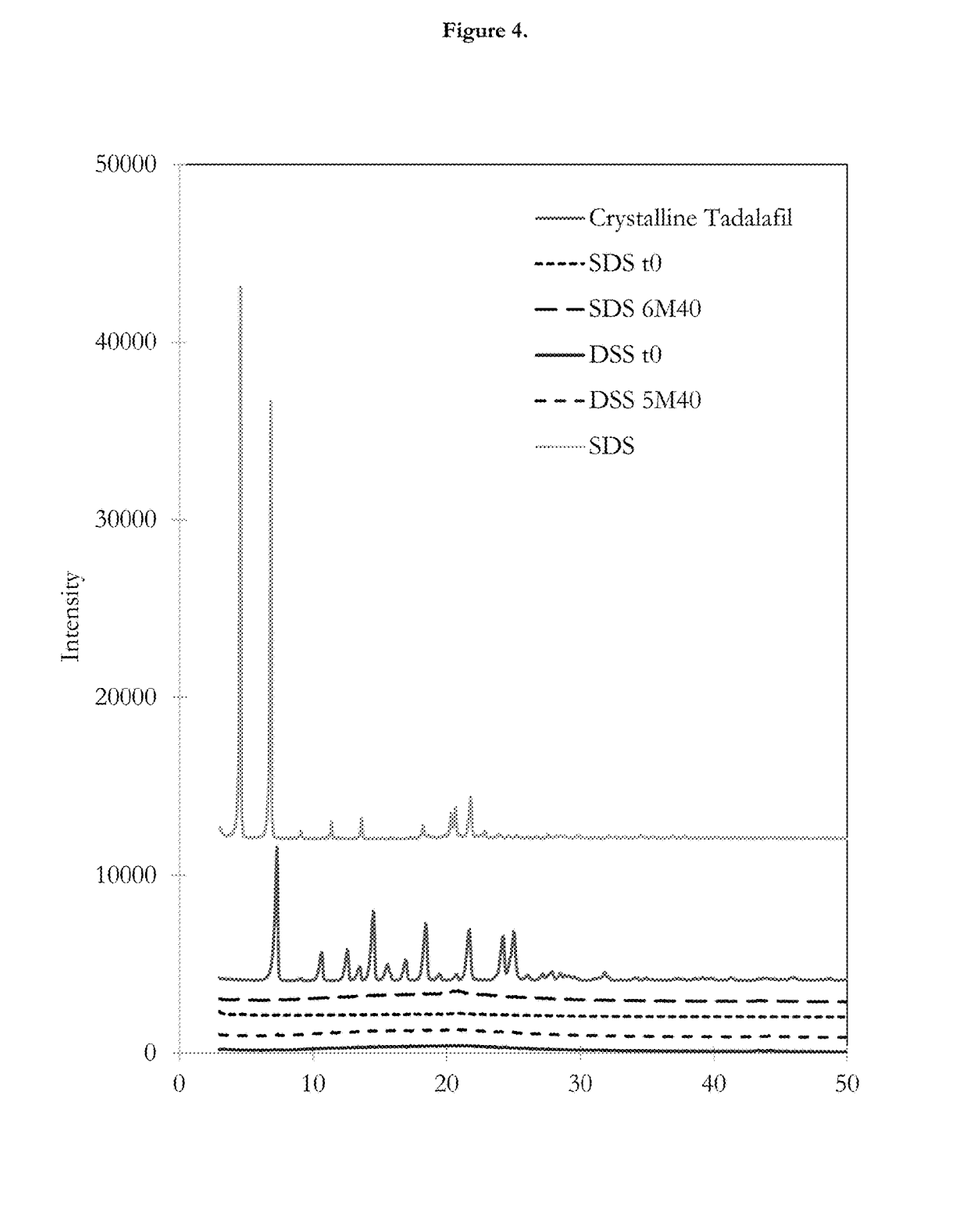
FIG. 4. shows pXRD diffractograms of unformulated crystalline Tadalafil, Tadalafil pharmaceutical formulation containing SDS right after the production (t0) and after 6 months storage at 40° C. (6M40), Tadalafil pharmaceutical formulation containing DSS right after the production (t0) and after 5 months storage at 40° C. (5M40) and crystalline SDS.
Figure 5:
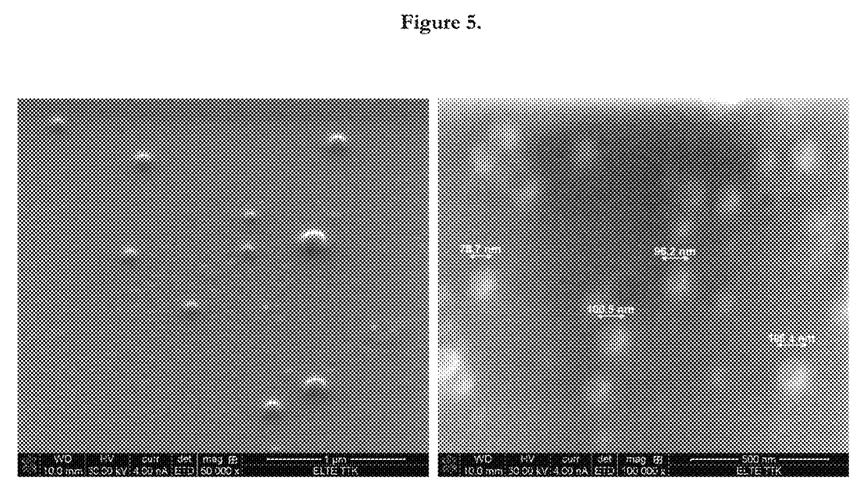
FIG. 5. shows SEM images of Tadalafil pharmaceutical formulation containing copovidone (copolymer of vinylpyrrolidone and vinyl acetate) and dioctyl sodium sulfosuccinate.

Powder X-ray diffraction (pXRD) was used to monitor the stability of the solid Tadalafil pharmaceutical formulation. pXRD was measured after storage the pharmaceutical formulations at different conditions. 1 month storage at 40° C./75% relative humidity showed no crystallization under any of the conditions tested (FIG. 4).

Structural Analysis

Morphology of Tadalafil pharmaceutical was investigated using FEI Quanta 3D scanning electron microscope. Tadalafil pharmaceutical formulation comprises spherical particles in the size range of less than 110 nm (FIG. 7).

Structural analysis was performed by using LabRAM HR UV-VIS-NIR spectrometer.

In an embodiment said Tadalafil pharmaceutical compositions are characterized by the Raman spectra shown in FIG. 6 and FIG. 7.

The structure of the Tadalafil pharmaceutical formulation was investigated by powder X-ray diffraction (XRD) analysis (Philips PW1050/1870 RTG powder-diffractometer). The measurements showed that the Tadalafil in the pharmaceutical formulations was XRD amorphous (See in FIG. 4). Characteristic reflections on the diffractograms of pharmaceutical Tadalafil formulation at 43 and 44 2Theta could be attributed to sample holder.

In-Vivo Pharmacokinetics
In-Vivo PK Test in Large Animals

A beagle dog study using the pharmaceutical compositions of Tadalafil at a dose of 20 mg/kg was performed in the fasted state. The pharmaceutical compositions were administered as a reconstituted dispersion. The absorption of Tadalafil was fast with $t_{max}$ values at 0.5-0.75 hours. The absorption of Tadalafil from Cialis® tablets was slow with $t_{max}$ values in the 2-4 hours range. When the pharmaceutical composition was administered the maximal plasma concentration measured for the Cialis® tablet was reached within 15 minutes (FIG. 9). Comparison of the results with published beagle dog pharmacokinetic data (at 10 mg/kg dose) indicates that the oral bioavailability of the granulated pharmaceutical compositions was 74% and 92% for composition comprising DSS and composition comprising SDS, respectively, while the oral bioavailability of Cialis was 33% (FIG. 10 and Table 3.). Table 3 shows the pharmacokinetic parameters following the oral administration of 20 mg Cialis® or the pharmaceutical formulations to beagle dogs in the fasted state (N=3).

TABLE 3

| Test article and route | Dose | $t_{max}$ (h) | $C_{max}$ (ng/ml) | $AUC_{24}$ (h*ng/ml) | Estimated F (%) |
|---|---|---|---|---|---|
| Cialis oral | 20 mg | 2-4 | 202 ± 66 | 1524 ± 667 | 33 |
| Tadalafil pharmaceutical formulation 1 oral | 20 mg | 0.5 | 539 ± 38 | 3373 ± 670 | 74 |
| Tadalafil pharmaceutical formulation 2 oral | 20 mg | 0.75 | 515 ± 71 | 4243 ± 977 | 93 |
| Tadalafil oral* | 10 mg/kg | 3 | 526 ± 281 | 4109 ± 3141 | 18 |
| Tadalafil iv* | 10 mg/kg | N.A. | 3663 ± 1228 | 22894 ± 4197 | 100 |

*http://www.accessdata.fda.gov/drugsatfda_docs/nda/2003/21-368_Cialis_Pharmr.pdf From the foregoing description, one skilled in the art can easily ascertain the essential characteristics, and without departing from the spirit and scope thereof, can make various changes and modifications to adapt it to various usages and conditions.

What is claimed is:

1. A pharmaceutical composition comprising
   10-40% by weight of Tadalafil or a salt thereof;
   35-70% by weight of a primary pharmaceutical excipient which is copovidone (copolymer of vinylpyrrolidone and vinyl acetate); and
   5-50% by weight of a secondary pharmaceutical excipient which is sodium lauryl sulfate;
   wherein said pharmaceutical composition is obtained by a process comprising mixing followed by spray-drying;
   wherein said pharmaceutical composition has a controlled particle size in the range between 10 nm and 500 nm; and
   wherein said pharmaceutical composition shows X-ray amorphous character in the solid form.

2. The pharmaceutical composition as recited in claim 1, wherein said composition is characterized by said Raman spectrum as shown in FIG. 7.

3. The pharmaceutical composition as recited in claim 1, wherein said particle size is between 10 nm and 200 nm.

4. The pharmaceutical composition as recited in claim 1, wherein said pharmaceutical composition shows a $t_{max}$ of 0.5-0.75 hours.

5. The pharmaceutical composition as recited in claim 1, wherein said pharmaceutical composition has a dissolution profile such that about 60% of the pharmaceutical composition is dissolved in simulated gastric fluid over two hours.

6. A pharmaceutical dosage form comprising the pharmaceutical composition according to claim 1, together with pharmaceutically acceptable excipients.

7. The pharmaceutical dosage form comprising the pharmaceutical composition according to claim 6, wherein said pharmaceutical dosage form is suitable for oral administration.

8. The pharmaceutical composition as recited in claim 1, wherein the pharmaceutical composition has an apparent solubility in water of at least 0.7 mg/mL.

9. The pharmaceutical composition as recited in claim 1, wherein the pharmaceutical composition has a PAMPA permeability of at least $4 \times 10^{-6}$ cm/s when dispersed in water, FaSSIF or FeSSIF biorelevant media, which does not decrease in time at least for 6 months.

* * * * *